US009056909B2

(12) United States Patent
Chu et al.

(10) Patent No.: US 9,056,909 B2
(45) Date of Patent: Jun. 16, 2015

(54) MYCOPLASMA HYOPNEUMONIAE AVIRULENT ADJUVANTED LIVE VACCINE

(75) Inventors: Hsien-Jue Chu, Bonner Springs, KS (US); Zhichang Xu, Fort Dodge, IA (US); Wumin Li, Fort Dodge, IA (US); Nicole Rae Gibson, Humboldt, IA (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 12/265,274

(22) Filed: Nov. 5, 2008

(65) Prior Publication Data

US 2009/0117152 A1    May 7, 2009

Related U.S. Application Data

(60) Provisional application No. 60/985,811, filed on Nov. 6, 2007.

(51) Int. Cl.
*A61K 39/02* (2006.01)
*C12N 1/02* (2006.01)
*C07K 14/30* (2006.01)
*A61K 39/116* (2006.01)
*A61K 39/00* (2006.01)

(52) U.S. Cl.
CPC ............. *C07K 14/30* (2013.01); *A61K 39/0241* (2013.01); *A61K 39/116* (2013.01); *A61K 2039/522* (2013.01); *A61K 2039/55566* (2013.01)

(58) Field of Classification Search
CPC .................................. A61K 39/02; C12N 1/02
USPC ...................................... 424/264.1; 435/252.1
See application file for complete search history.

(56) References Cited

U.S. PATENT DOCUMENTS

| | | | |
|---|---|---|---|
| 3,917,619 | A | 11/1975 | Yoshioka et al. |
| 4,824,785 | A | 4/1989 | Acree et al. |
| 4,894,332 | A | 1/1990 | Schaller et al. |
| 6,001,348 | A | 12/1999 | Witvliet |
| 7,056,492 | B2 | 6/2006 | Goudie et al. |
| 7,276,353 | B2 | 10/2007 | Meng et al. |
| 7,279,166 | B2 | 10/2007 | Meng et al. |
| 2003/0017171 | A1 | 1/2003 | Chu et al. |
| 2003/0091595 | A1 | 5/2003 | Chu |
| 2003/0170270 | A1 | 9/2003 | Meng et al. |
| 2004/0253270 | A1 | 12/2004 | Meng et al. |
| 2005/0053627 | A1 | 3/2005 | Leonard et al. |

FOREIGN PATENT DOCUMENTS

| | | |
|---|---|---|
| CA | 2208790 | 6/1997 |
| EP | 283840 A2 | 9/1988 |
| EP | 0571648 A1 | 1/1993 |
| JP | S62-273456 | 11/1987 |
| WO | 8600019 A1 | 1/1986 |
| WO | 9203157 | 3/1992 |
| WO | 9817310 | 4/1998 |
| WO | WO 02/10343 A | 2/2002 |
| WO | 0249666 A2 | 6/2002 |
| WO | 03003941 A2 | 1/2003 |
| WO | 03024354 A2 | 3/2003 |
| WO | 03086473 A1 | 10/2003 |
| WO | WO2004/058142 A2 | 7/2004 |
| WO | WO 2004/058142 A2 | 7/2004 |
| WO | 2004080400 A2 | 9/2004 |

OTHER PUBLICATIONS

Etheridge et al., *A Method for Assessing Induced Resistance to Enzootic Pneumonia of Pigs*. Res. Vet. Sci. (1982) 33:188-191.
Kristensen et al., *Cell-Mediated and Humoral Immune Response in Swine After Vaccination and Natural Infection with Mycoplasma hyopneumoniae*. Am. J. Vet. Res. (1981) 42:784-788.
Ross et al., *Characteristics of protective activity of Mycoplasma hyopneumoniae vaccine*. Am. J. Vet. Res. (1984) 45:1899-1905.
Amaral de Castro et al., *Variable number of tandem aminoacid repeats in adhesion-related CDS products in Mycoplasma hyponeumoniae strains*. Veterinary Microbiology. (2006) 116:258-269.
Vasconcelos et al., *Swine and Poultry Pathogens: the Complete Genome Sequences of Two Strains of Mycoplasma hyopneumoniae and a Strain of Mycoplasma synoviae..* J. Bacteriol. (2005) 187(16):5568-5577.
Djordjevic et al., *Proteolytic Processing of the Mycoplasma hyopneumoniae Cilium Adhesin*. Infection and Immunity. (2004) 72(5):2791-2802.
King et al., *Immunofluorescence of Feline Panleucopenia Virus in Cell Culture: Determination of Immunological Status of Felines by Serum Neutralization*. Journal of Comparative Medicine and Vet. Science, (1965) 29: 85-89.
Thacker et al., *Mycoplasma hyopneumoniae Potentiation of Porcine Reproductive and Respirator Syndrome Virus-Induced Pneumonia*. J. Clin. Microbiol. (1999) 37(3):620-627.
International Search Report dated Feb. 6, 2009.

(Continued)

*Primary Examiner* — Jennifer Graser
(74) *Attorney, Agent, or Firm* — Gloria K. Szakiel; Barbara L. Renda

(57) ABSTRACT

Provided are immunogenic and vaccine compositions and methods for their preparation and use, which compositions are effective in protecting against, minimizing the severity of, preventing, and/or ameliorating M. hyopneumoniae infection. Administration to an animal of one or two doses of an adjuvanted live avirulent M. hyopneumoniae composition disclosed herein is effective in providing immunity to the animal and protection from infection with a virulent strain of M. hyopneumoniae thereby reducing the severity of and/or preventing disease caused by one or more virulent strain of M. hyopneumoniae. Also provided are compositions, which further comprise one or more antigen such as, for example, one or more live bacteria, bacterin, toxoid, and/or virus and/or viral antigen. Exemplified are immunogenic compositions, comprising an adjuvanted live avirulent M. hyopneumoniae and compositions, comprising Porcine Circovirus Type 1-Type 2 chimera modified live vaccine (cPCV1-2) in further combination with an adjuvanted live avirulent M. hyopneumoniae.

23 Claims, No Drawings

(56) References Cited

OTHER PUBLICATIONS

Morrow C J et al: "Production of Temperature-Sensitive Clones of Mycoplasma Synoviae for Evaluation as Live Vaccines" Avian Diseases, American Association of Avian Pathologists, Kennet SQ., PA, US, vol. 42, Jan. 1, 1993, pp. 687-870.

Lai W C et al: "Biologioal Evaluation of Mycoplasma-Pulmonis Temperature-Senstive Mutants for Use as Possible Rodent Vaccines" Infection and Immunity, American Society for Microbiology. Washington, vol. 58, No. 7, Jul. 1, 1990, pp. 2289-2296.

Javed Mohammed A et al: "Correlates of immune protection in chickens vaccinated with Mycoplasma gallisepticum strain GT5 following challenge with pathogenic M-gallisepticum strain R-low" Infection and Immunity, American Society for Microbiology. Washington, vol. 73, No. 9, Sep. 1, 2005, pp. 5410-5419.

Evans R D et al: "Evaluation OP a Mycoplasma-Gallisepticum Strain Exhibiting Reduced Virulence for Prevention and Control of Poultry Mycoplasmosis" Avian Diseases, American Association of Avian Pathologists, Kennet SQ., PA, US, vol. 36, No. 2, Jan. 1, 1992, pp. 197-201.

Alessandri Enrico et al: "Field trials with the use of a live attenuated temperature-sensitive vaccine for the control of Mycoplasma gallisepticum infection in meat-type turkeys" Italian Journal of Animal Science,, vol. 4, No. 3, Jul. 1, 2005, pp. 282-286.

Fort Dodge Australia (2000) TechNote—Technical Update TF S04-00 (1) "Suvaxyn M.Hyo—How it works".

J. Tully and R.F. Whitcomb (volume editors) Mycoplasmas vol. 2: Human and Animal Mycoplasmas (1979), pp. 142-143.

Minion et al. "The Genome Sequence of Mycoplasma hyopneumoniae Strain 232, the Agent of Swine Mycoplasmosis", Journal of Bacteriology, vol. 186, No. 21, (2004) pp. 7123-7133.

Blank et al. "A physical and genetic map of the Mycoplasma hyopneumoniae strain J genome" Canadian Journal of Microbiology, vol. 46, (2000), pp. 832-840.

Petrovsky et al. "Vaccine adjuvants: Current state and future trends" Immunology and Cell Biology, vol. 82, (2004). pp. 488-496.

Bouh et al, "Monoclonal Antibodies to *Escherichia coli*-Expressed P46 and P65 Membranous Proteins for Specific Immunodetection of Mycoplasma hyopneumoniae in Lungs of Infected Pigs", Clinical and Diagnostic Laboratory Immunology, vol. 10 No. 3, May 2003, pp. 459-468.

Burnett et al. "P159 is a proteolytically processed, surface adhesin of Mycoplasma hyopneumonia defined domains of P159 bind heparin and promote adherence to eukaryote cells", Molecular Microbiology (Mar. 13, 2006) 60(3), 669-686.

MYCOPLASMA HYOPNEUMONIAE AVIRULENT ADJUVANTED LIVE VACCINE

CROSS-REFERENCE TO RELATED APPLICATIONS

This application claims the benefit under 35 U.S.C. §119(e) of U.S. Provisional Application No. 60/985,811 filed on Nov. 6, 2007, the disclosure of which is incorporated by reference herein in its entirety.

FIELD OF THE INVENTION

The present disclosure relates generally to the fields of immunology and veterinary medicine. More specifically, the present disclosure provides adjuvanted live avirulent *M. hyopneumoniae* compositions based on a J strain of *M. hyopneumoniae*, including immunogenic or vaccine compositions, which aid in reducing the severity of and/or in preventing disease caused by one or more virulent strain of *M. hyopneumoniae*. Also provided are adjuvanted live avirulent *M. hyopneumoniae* compositions, including immunogenic or vaccine compositions, further comprising Porcine Circovirus Type 1-Type 2 chimera modified live vaccine (cPCV1-2). One or two-dose administration to an animal of an adjuvanted live avirulent *M. hyopneumoniae* composition disclosed herein is effective in providing immunity, including cell-mediated immunity and/or humoral immunity, from infection with a virulent strain of *M. hyopneumoniae*.

BACKGROUND OF THE INVENTION

*Mycoplasma hyopneumoniae* (also referred to as *M. hyopneumoniae*) is the etiologic agent of swine mycoplasmal pneumonia. The disease causes a chronic cough, dull hair coat, retarded growth and unthrifty appearance lasting several weeks. Characteristic lesions of purple to gray areas of consolidation, particularly in ventral apical and cardiac lobes are observed in infected animals. Although the disease causes little mortality, affected swine are often prone to secondary infections by opportunistic pathogens, resulting in death or stress. (R. F. Ross, Mycoplasmal diseases, pp. 436-444, in A. D. Laman, et al., (eds.) Diseases of Swine, Iowa State University Press, 1986).

The disease is believed to be one of the most important causes of disease-associated loss in swine (Whittlestone, pp. 133-176, in Tully and Whitcomb (eds.), The *Mycoplasma* Vol 2: Human and Animal Mycoplasmas, New York, Academic Press, (1979)). The disease generally results in inefficient weight gainers, and in stunted and sickly animals. Also, affected swine are often prone to secondary infection by opportunistic organisms (Burch, Pig America pp. 26-27, December, 1982). The economic impact of the disease is significant. Economic losses alone have been estimated at between 200 to 250 million dollars annually.

*Mycoplasma hyopneumoniae* is a slow growing, fastidious bacterium that lacks a cell wall. It is frequently difficult to isolate from the respiratory tract due to *Mycoplasma hyorhinis*, a common secondary agent also located in the respiratory tract. The disease is spread by aerosol, produced by coughing, and by direct contact from an affected or convalescent carrier swine. Mingling of infected animals and uninfected animals results in early and frequent reinfection. Infection frequently starts with infection of piglets by carrier sows at farrowing.

Due to herd management techniques, infection may not become evident until later in life. Additional infection usually is observed after weaning when pigs are pooled. Overt disease is normally observed in pigs at six weeks of age or older. Growth rates and feed conversion rates are markedly reduced in affected animals. Existing treatments using antibiotics are expensive and require prolonged use. Animal reinfection remains a problem.

Thus, vaccines are presently the most effective method for avoiding infections and their consequences. There have been numerous attempts to provide a vaccine for protecting swine against *Mycoplasma hyopneumoniae* infection. Several investigators have disclosed vaccines comprising recombinantly produced surface antigens of *Mycoplasma hyopneumoniae*, Schaller et al., U.S. Pat. No. 4,894,332, issued Jan. 16, 1990; European Patent Publication No. 283,840, published Sep. 28, 1988. PCT Publication No. WO 86/00019, published Jan. 3, 1986, discloses a *Mycoplasma hyopneumoniae* vaccine comprising exclusively *Mycoplasma hyopneumoniae* plasma membranes, free of other cell components. Etheridge et al., Res. Vet. Sci. 33:188 (1982), found incomplete protection against lung colonization by *Mycoplasma hyopneumoniae* when a live vaccine was given intravenously, subcutaneously, or intraperitoneally. Kristensen et al., Am. J. Vet. Res. 42:784 (1981), found no protection of swine against mycoplasmal pneumonia after injection with heat-inactivated *Mycoplasma hyopneumoniae*. Ross et al., Am. J. Vet. Res. 45:1899 (1984), found that use of *Mycoplasma hyopneumoniae* extracts prepared by a freeze-thaw procedure to immunize swine, provided only variable protection, and in some instances, enhanced lesion development was noted in immunized swine. These investigators also studied a whole-cell vaccine prepared by formalin inactivation. Formalin inactivation significantly hindered the protective immunogenicity of *Mycoplasma hyopneumoniae*, and this vaccine was not effective. Yoshioka et al., U.S. Pat. No. 3,917,819 (issued Nov. 4, 1975) discloses several killed Mycoplasma vaccines comprising Mycoplasma inactivated with formalin, including an inactivated vaccine for *Mycoplasma hyopneumoniae*. Chung-Nan European Patent Publication 571,648 disclosed an *M. hyopneumoniae* vaccine based on the highly proliferative and antigenic strain PRIT-5.

Vaccines based on inactivated virulent *Mycoplasma hyopneumoniae* strains are commercially available. Fort Dodge Animal Health (FDAH) markets *Mycoplasma hyopneumoniae* bacterin under the name Suvaxyn® and Respifend® *Mycoplasma hyopneumoniae* for use as a vaccine to protect healthy swine against clinical signs caused by *Mycoplasma hyopneumoniae*. This bacterin vaccine is recommended as a two-dose vaccine for pigs at least one-week old, with the second dose two to three weeks after the first vaccination.

The *M. hyopneumoniae* J strain is a non-pathogenic strain with reduced capacity to adhere to porcine cilia and, therefore, to cause disease. Castro et al., *Veterinary Microbiology* 116:258-269 (2006) and Vasconcelos et al, *J. Bacteriol.* 187 (16):5568-5577 (2005) (describing the complete genome sequence of *M. hyopneumoniae* J strain (ATCC 25934)). Genomic comparisons between pathogenic and nonpathogenic strains (J strain) have revealed variations in surface proteins, including cilium adhesin, that are believed to be determinative of relative pathogenic properties between *M. hyopneumoniae* strains. Vasconcelos et al. (2006) and Djordjevic et al., *Infection and Immunity* 72(5):2791-2802 (2004).

*M. hyopneumonia* expresses, on its cell surface, membranous lipoproteins, particularly the P46, P65, and P97 proteins, which carry species-specific antigenic determinants. Recently, Bouh et al. described monoclonal antibodies to P46 and P65 of live avirulent *M. hyopneumoniae* reference J strain ATCC 25934. *Clin. Diag. Lab. Immunology* 10(3):459-468 (2003). Blank and Stemke described a physical and genetic map of *M. hyopneumoniae* strain J genome, *Can. J. Microbiol.* 46:832-840 (2000), and Wilton et al. described the screening of expression libraries generated from the non-pathogenic *M. hyopneumoniae* J strain and the screening of those libraries with porcine hyperimmune antiserum against *M. hyopneumoniae*.

There is a need for compositions, including immunogenic or vaccine compositions, made from live adjuvanted avirulent *Mycoplasma hyopneumoniae*, which compositions provide efficacy against virulent strains of *M. hyopneumoniae*. The citation of any reference herein should not be deemed as an admission that such reference is available as prior art to the instant invention.

SUMMARY OF THE INVENTION

The present disclosure provides compositions, including immunogenic compositions or vaccine compositions, comprising an immunologically effective amount of a live avirulent *Mycoplasma hyopneumoniae* and a biologically acceptable adjuvant. Compositions disclosed herein elicit an immune response against *Mycoplasma hyopneumoniae*, thereby preventing and/or minimizing the severity of disease caused by this organism or ameliorating at least one symptom associated with the disease.

Accordingly, in one aspect, the invention provides a composition for eliciting an anti-*Mycoplasma hyopneumoniae* immune response in an animal, said composition comprising an immunologically effective amount of a live avirulent strain of *Mycoplasma hyopneumoniae* and a biologically acceptable adjuvant.

In one embodiment, the composition comprises a live avirulent strain of *Mycoplasma hyopneumoniae* whose genome comprises a nucleic acid sequence having at least about 90% homology to the nucleic acid sequence of a reference J strain.

In one embodiment, the composition comprises a live avirulent strain of *Mycoplasma hyopneumoniae* whose genome comprises a nucleic acid sequence having at least about 95% homology to the nucleic acid sequence of a reference J strain.

In one embodiment, the composition comprises a live avirulent strain of *Mycoplasma hyopneumoniae* whose genome comprises a nucleic acid sequence having at least about 99% homology to the nucleic acid sequence of a reference J strain.

In one embodiment, the composition comprises a live avirulent strain of *Mycoplasma hyopneumoniae* that has at least about 70% polymorphic identity to a reference J strain.

In one embodiment, the composition comprises a live avirulent strain of *Mycoplasma hyopneumoniae* that has at least about 85% polymorphic identity to a reference J strain.

In one embodiment, the composition comprises a live avirulent strain of *Mycoplasma hyopneumoniae* that has at least about 95% polymorphic identity to a reference J strain.

In one embodiment, the percent homology of the live avirulent strain of *Mycoplasma hyopneumoniae* used in the compositions described herein are determined by comparison to an avirulent reference J strain having ATCC accession number 25934 (GenBank Accession Number AE017243) or 27715. In other certain embodiments, the reference strain may be a strain that is a virulent strain, for example, those having ATCC accession numbers 25617 or 25095.

In one embodiment, the percent polymorphic identity of the live avirulent strain of *Mycoplasma hyopneumoniae* used in the compositions described herein are determined by comparison to an avirulent reference J strain having ATCC accession number 25934 or 27715. In other certain embodiments, the reference strain may be a strain that is a virulent strain, for example, those having ATCC accession numbers 25617 or 25095.

In one embodiment, the live avirulent strain of *Mycoplasma hyopneumoniae* used in the compositions described herein is a J strain designated as ATCC accession number 25934 or 27715.

In one embodiment, the live avirulent strain of *Mycoplasma hyopneumoniae* used in the compositions described herein is a J strain designated as ATCC accession number 27715.

In one embodiment, the immune response elicited by a live-avirulent strain of *Mycoplasma hyopneumoniae* protects an animal against infection with, or reduces the severity of at least one symptom associated with an infection by a virulent strain of *Mycoplasma hyopneumoniae*.

In one embodiment, one-dose administration to an animal of an adjuvanted live avirulent *M. hyopneumoniae* composition disclosed herein is effective in providing immunity to the animal from Mycoplasma infection.

In one embodiment, two-dose administration to an animal of an adjuvanted live avirulent *M. hyopneumoniae* composition disclosed herein is effective in providing immunity to the animal from *Mycoplasma* infection.

Adjuvanted live avirulent *Mycoplasma hyopneumoniae* vaccine compositions disclosed herein may be suitably employed for use in swine against infection and disease caused by *Mycoplasma hyopneumoniae* and will find utility in managing and/or preventing the spread of infection and disease caused by *Mycoplasma hyopneumoniae* in swine populations.

Thus, immunogenic compositions and vaccine compositions of the present disclosure employ one or more live avirulent *Mycoplasma hyopneumoniae* in combination with one or more adjuvant such as a biologically acceptable adjuvant. The biologically acceptable adjuvant may, optionally, be one or more adjuvant(s) selected from the group consisting of SP-Oil, SL-CD, an acrylic acid polymer (such as Carbopol®, Noveon, Inc., Cleveland, Ohio), and a mixture of a metabolizable oil such as one or more unsaturated terpene hydrocarbon(s), for example squalene or squalane, and a polyoxyethylene-polypropylene block copolymer such as Pluronic® (BASF, Florham Park, N.J.).

The concentration of adjuvant employed in the compositions described herein will depend upon the nature of the adjuvant. Adjuvants are typically present in the compositions described herein at a final concentration of about 1-50% (v/v) and more typically at a final concentration of about 10%, 15%, 20%, 25%, or 30% (v/v). In compositions comprising SP-Oil, the adjuvant is typically present at between about 1% and about 25% (v/v), more typically between about 5% and about 15% (v/v) such as, for example, at about 10% (v/v). In compositions comprising an acrylic acid polymer and a mixture of a metabolizable oil that comprises one or more terpene hydrocarbon(s) and a polyoxyethylene-polypropylene block copolymer, the ratio of acrylic acid polymer to metabolizable oil/polyoxyethylene-polypropylene block copolymer mixture is typically in a ratio of between about 1:25 and about 1:50 and typically at a final concentration of between about 1% and about 25% (v/v).

In one embodiment, the biologically acceptable adjuvant comprises SP-Oil. In one embodiment, the SP-Oil is present at a concentration of between about 1% and about 25% v/v. In one embodiment, the SP-Oil is present at a concentration of between about 5% and about 15% v/v. In one embodiment, the SP-Oil is present at a concentration of about 10% v/v.

Within certain embodiments, compositions disclosed herein may employ, in further combination, one or more other live bacteria, bacterin, toxoid, and/or viral antigen. Thus, within certain aspects of these embodiments, the adjuvanted live avirulent *M. hyopneumoniae* composition may comprise an immunologically effective amount of live avirulent *Mycoplasma hyopneumoniae* and one or more biologically acceptable adjuvant(s) in further combination with (a) one or more live bacteria; (b) one or more bacterin; (c) one or more purified toxoid from one or more pathogens such as, for example, *Haemophilus parasuis, Pasteurella multocida, Streptococcus suis, Actinobacillus pleuropneumoniae, Bordetella bronchiseptica, Salmonella choleraesuis, Erysipelothrix rhusiopathiae* and leptospira bacteria; and/or (d) one or more viral antigen wherein the virus is selected from the group consisting of swine influenza virus (SIV), porcine reproductive and respiratory syndrome virus (PRRSV), raccoon poxvirus expressing PRRS and/or other antigens, TGEV expressing PRRS and/or other antigens, and porcine circovirus (PCV). Within certain aspects of these embodiments, exemplified herein are compositions, including immunogenic compositions or vaccine compositions, which employ, in further combination, Porcine Circovirus Type 1-Type 2 chimera modified live vaccine (cPCV1-2). Within these or alternative embodiments, compositions, including immunogenic or vaccine compositions, may additionally or optionally include a preservative and stabilizer such as, for example, SGGK, thimerosol and/or EDTA.

The concentration of such other live bacteria, bacterin, toxoid, and/or viral antigen employed in the compositions described herein will depend upon the nature of the live bacteria, bacterin, toxoid, and/or viral antigen and are typically present in the compositions described herein. For such compositions wherein the other antigen is bacterial, the bacteria are typically present at a final concentration of between about $0.5 \times 10^5$ to $0.5 \times 10^{10}$ per milliliter. Alternatively, the bacteria are present at a final concentration of between about $0.5 \times 10^6$ to $0.5 \times 10^9$ per milliliter or at a final concentration of between about $0.5 \times 10^7$ to $0.5 \times 10^8$ per milliliter.

A second aspect of the invention provides methods for generating an immune response to *Mycoplasma hyopneumoniae*, or for protecting an animal against disease caused by *Mycoplasma hyopneumoniae* and/or for preventing or ameliorating an outbreak of such disease among animal populations by administering an adjuvanted live avirulent *Mycoplasma hyopneumoniae* composition as described herein. In a related aspect, the present disclosure also provides methods for enhancing an immune response to *Mycoplasma hyopneumoniae*. Such methods comprise the steps of administering to an animal, such as swine, in one or two doses, a composition comprising one or more adjuvanted live avirulent *Mycoplasma hyopneumoniae* strain.

In one embodiment the methods of the present invention use a live avirulent strain of *Mycoplasma hyopneumoniae* whose genome comprises a nucleic acid sequence having about 90% homology to the nucleic acid sequence of a reference J strain.

In one embodiment the methods of the present invention use a live avirulent strain of *Mycoplasma hyopneumoniae* whose genome comprises a nucleic acid sequence having about 95% homology to the nucleic acid sequence of a reference J strain.

In one embodiment the methods of the present invention use a live avirulent strain of *Mycoplasma hyopneumoniae* whose genome comprises a nucleic acid sequence having about 99% homology to the nucleic acid sequence of a reference J strain.

In one embodiment the methods of the present invention use a live avirulent strain of *Mycoplasma hyopneumoniae* that has at least about 70% polymorphic identity to a reference J strain.

In one embodiment the methods of the present invention use a live avirulent strain of *Mycoplasma hyopneumoniae* that has at least about 85% polymorphic identity to a reference J strain.

In one embodiment, the methods of the present invention use a live avirulent strain of *Mycoplasma hyopneumoniae* that has at least about 95% polymorphic identity to a reference J strain.

In one embodiment, the live avirulent strain of *Mycoplasma hyopneumoniae* used in the methods of the invention, as described herein, is a J strain designated as ATCC accession number 25934 or 27715.

In one embodiment, the live avirulent strain of *Mycoplasma hyopneumoniae* used in the methods of the invention, as described herein, is a J strain designated as ATCC accession number 27715.

In one embodiment, the invention provides a method for enhancing an immune response to *Mycoplasma hyopneumoniae*, the method comprising the steps of:
  a) at a first time, administering a first immunogenic composition comprising an immunologically effective amount of a live avirulent *Mycoplasma hyopneumoniae* strain adjuvanted with a biologically acceptable adjuvant material to an animal;
  b) at a second time, administering a second immunogenic composition comprising an immunologically effective amount of a live avirulent *Mycoplasma hyopneumoniae* adjuvanted with a biologically acceptable adjuvant material to an animal.

In certain embodiments, depending upon the precise application contemplated, compositions may be administered parenterally, such as through intramuscular, subcutaneous, or intraperitoneal injection, or by topical application of a cream. Alternatively, compositions may be administered through aerosol, intranasal, or oral routes, such as by intranasal spray or oral administration by hand delivery or mass application.

These and other embodiments, features and advantages of the invention will become apparent from the detailed description and the appended claims set forth herein below. All patents, patent applications, and other literature cited herein are hereby incorporated by reference in their entirety. In the case of inconsistencies, the present disclosure will prevail.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Accordingly, in the present application, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

Although any methods and materials similar or equivalent to those described herein can be used in the practice or testing of the invention, the preferred methods and materials are now described. All publications mentioned herein are incorporated by reference in their entirety.

Definitions

The terms used herein have the meanings recognized and known to those of skill in the art, however, for convenience and completeness, particular terms and their meanings are set forth below.

The term "about" or "approximately" means within a statistically meaningful range of a value. Such a range can be within an order of magnitude, typically within 50%, more typically within 20%, more typically still within 10%, and even more typically within 5% of a given value or range. The allowable variation encompassed by the term "about" or "approximately" depends on the particular system under study, and can be readily appreciated by one of ordinary skill in the art.

"Adjuvant" means a composition comprised of one or more substances that enhances the antigenicity of live avirulent *Mycoplasma hyopneumoniae* in a composition, typically a vaccine composition. An adjuvant can serve as a tissue depot that slowly releases the antigen and also as a lymphoid system activator that non-specifically enhances the immune response (Hood, et al., *Immunology, Second Ed.*, Menlo Park, Calif.: Benjamin/Cummings, 1984. p. 384). Often, a primary vaccination with an antigen alone, in the absence of an adjuvant, will fail to elicit a humoral or cellular immune response. Adjuvants include, but are not limited to, complete Freund's adjuvant, incomplete Freund's adjuvant, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxypholoxy)-ethylamine, BCG (bacille Calmette-Guerin) and *Corynebacterium parvum*. Preferably, the adjuvant is biologically acceptable.

Adjuvants employed in the compositions described herein are typically "biologically acceptable adjuvants" and, thus, may be used in combination with live avirulent *Mycoplasma hyopneumoniae* such that the resulting compositions may be administered in vivo without concomitant toxicity to an animal. Exemplified herein are compositions including live avirulent *Mycoplasma hyopneumoniae* in combination with one or more biologically acceptable adjuvant selected from the group consisting of SP-Oil, SL-CD, Carbopol, and a mixture of a metabolizable oil such as one or more unsaturated terpene hydrocarbon(s), for example squalene or squalane, and a polyoxyethylene-polypropylene block copolymer such as Pluronic®.

A live aviruient *Mycoplasma hyopneumoniae* strain or molecule therefrom is "antigenic" when it is capable of specifically interacting with an antigen recognition molecule of the immune system, such as an immunoglobulin (antibody) or T cell antigen receptor. Typically, an antigenic molecule is a polypeptide, or variant thereof, which contains an "epitope" of at least about five and typically at least about 10 amino acids. An antigenic portion of a polypeptide, also called herein the "epitope," can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

The term "at least" means not less than.

As used herein, a "bacterin" is a bacterium harvest that has been inactivated and that, in combination with certain adjuvants, can elicit protective immunity to protect against disease or infection when administered to animals.

Acrylic acid polymers are typically carbomers. Carbomers are commercially available under the trade name "Carbopol" and are described, for example, in U.S. Pat. Nos. 2,909,462 and 3,790,665, each of which is incorporated herein by reference.

The term "carrier" refers to a diluent, adjuvant, excipient, stabilizer, preservative, and/or vehicle with which a compound or composition is administered. Such carriers can be sterile liquids, such as water and oils, including those of petroleum, animal, vegetable or synthetic origin, such as peanut oil, soybean oil, mineral oil, sesame oil and the like. Water or aqueous solution saline solutions, for example, phosphate-buffered saline, Ringer's solutions and aqueous dextrose and glycerol solutions are frequently employed as carriers, particularly for injectable solutions. The carrier or diluent must be non-toxic and must not affect the biological activity of the antigen/immunogen. Other additional auxiliary substances, such as wetting or emulsifying agents, surfactants, pH buffering substances and the like may also be used in the compositions of the invention. Preservatives may include, for example, thimerosol and/or EDTA. Suitable pharmaceutical carriers are described in "Remington's Pharmaceutical Sciences" by E. W. Martin, 18$^{th}$ Edition. A wide variety of carriers are well known in the art, and the selection of specific carriers is well within the level of those skilled in the art.

The term "colony forming unit" or "CFU" is a unit of measure used to indicate the number of organisms capable of replication in a given sample. This is based on the theory that a colony is derived from the replication of a pair/cluster or single cell of bacteria.

The "immunologically effective amount" is the amount of live avirulent *Mycoplasma hyopneumoniae* that will elicit an immune response against *Mycoplasma hyopneumoniae*. The "immunologically effective amount" will depend upon the species, breed, age, size, health status of the recipient animal and will be influenced by the previous exposure of the animal to one or more strain of *Mycoplasma hyopneumoniae* whether that one or more strain is a virulent strain or an avirulent strain of *Mycoplasma hyopneumoniae*. As used herein, an "immunologically effective amount" of live avirulent *Mycoplasma hyopneumoniae*, when employed in combination with a suitable adjuvant, is that amount of *Mycoplasma hyopneumoniae* that is sufficient to enhance the immunogenicity of the live avirulent *Mycoplasma hyopneumoniae* and thus provides for protective immunity against challenge with a virulent *Mycoplasma hyopneumoniae* strain. In one embodiment, an immunologically effective amount is a minimum of about 1×10³ organisms. In one embodiment, an immunologically effective amount ranges from about 1×10³ colony forming units/ml (CFU/ML) to about 1×10¹¹ CFU/ML. In one embodiment, an immunologically effective amount is about 5×10⁷ CFU/ML.

As used herein, the term "immunogenic" means that the live avirulent *Mycoplasma hyopneumoniae* is capable of eliciting a humoral and/or cellular immune response. An immunogenic strain is also antigenic. An immunogenic composition is a composition that elicits a humoral and/or cellular immune response when administered to an animal.

The term "immunogenic composition" relates to any pharmaceutical composition containing an antigen, eg. a microorganism, which composition can be used to elicit an immune response in a mammal. The immune response can include a T cell response, a B cell response, or both a T cell and B cell response. The composition may serve to sensitize the mammal by the presentation of antigen in association with MHC molecules at the cell surface. In addition, antigen-specific T-lymphocytes or antibodies can be generated to allow for the future protection of an immunized host. An "immunogenic composition" may contain a live, attenuated, or killed/inactivated vaccine comprising a whole microorganism or an immunogenic portion derived therefrom that induces either a cell-mediated (T cell) immune response or an antibody-mediated (B cell) immune response, or both, and may protect the animal from one or more symptoms associated with infection by the microorganism, or may protect the animal from death due to the infection with the microorganism.

As used herein, the term "isolated" means that the referenced material is removed from its native environment. Thus, an isolated biological material can be free of some or all cellular components, i.e., components of the cells in which the native material occurs naturally (e.g., cytoplasmic or membrane component). A material is isolated if it is present in a cell extract or supernatant. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

As used herein, the term "MHDCE" designates *Mycoplasma hyopneumoniae* DNA cell equivalents and is defined as a unit of measure used to determine the approximate number of *Mycoplasma hyopneumoniae* organisms present in a given sample.

The term "parenteral administration" as used herein means administration by some other means than through the gastrointestinal tract, particularly to the introduction of substances into an organism by intravenous, subcutaneous, intramuscular, or intramedullary injection, but also to other non-oral and non-nasal routes of administration such as intraperitoneal injection or topical application.

The term "polymorphic identity to a reference J strain" refers to similarity between the protein expression profile of one non-J strain *Mycoplasma hyopneumoniae* to a reference J strain of *Mycoplasma hyopneumoniae*. The polymorphic identity may be based on one or more characteristics of one or more proteins, including, but not limited to, for example, the amount or size of one or more proteins of the *Mycoplasma hyopneumoniae* microorganism under investigation, to the sedimentation rate of one or more proteins, or to changes in the physical or biochemical characteristics of one or more proteins. The term may also include similarity between the nucleotide sequences that encode any one or more proteins of one non-J strain of *Mycoplasma hyopneumoniae* and a reference J strain of *Mycoplasma hyopneumoniae* and includes any mutations in these sequences, including deletions or substitutions. The change in the nucleotide or amino acid sequence is one that allows for retention of the avirulent nature of the *Mycoplasma hyopneumoniae* organism. A wide variety of assays for observing perturbations in nucleotide and amino acid sequences are well known in the art. For example, the size and structure of nucleic acid or amino acid sequences are observed by the Northern, Southern, Western, SDS-PAGE ELISA profiling, PCR and DNA sequencing protocols as known to those skilled in the art (see, e.g. Calus, D. et al. Veterinary Microbiology, Vol. 120, Issues 3-4, Mar. 10, 2007, pages 284-291; Scarman, A L, et al. Microbiology (1997), Vol. 143: 663-673). In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952,170 issued 17 Jan. 1995).

The term "purified" as used herein refers to material that has been isolated under conditions that reduce or eliminate the presence of unrelated materials, i.e., contaminants, including native materials from which the material is obtained. For example, a purified bacteria or protein is typically substantially free of host cell or culture components, including tissue culture or egg proteins, non-specific pathogens, and the like. As used herein, the term "substantially free" is used operationally, in the context of analytical testing of the material. Typically, purified material substantially free of contaminants is at least 50% pure; more typically at least 90% pure, and more typically still at least 99% pure. Purity can be evaluated by chromatography, gel electrophoresis, immunoassay, composition analysis, biological assay, and other methods known in the art. Methods for purification are well-known in the art. The term "substantially pure" indicates the highest degree of purity which can be achieved using conventional purification techniques known in the art.

A "reference strain" refers to a strain of microorganism, for example, *Mycoplasma hyopneumoniae*, that is obtained from a reliable source and which may be used as a control strain for which comparisons with other unestablished or unknown cultures may be compared. In the present invention, the reference strains of *Mycoplasma hyopneumoniae* may be avirulent J strains that are obtained from the American Type Culture Collection (ATCC) and are assigned ATCC accession numbers 25934 and 27715. In the present invention, these "reference strains" having ATCC accession numbers 25934 or 27715 have also been used to prepare the immunogenic compositions of the invention. In other certain embodiments of the present invention, the reference strains of *Mycoplasma hyopneumoniae* may be obtained from the American Type Culture Collection (ATCC) and are assigned ATCC accession numbers 25617 and 25095.

The term "SL-CD" refers to a sulpholipo-cyclodextrin that falls within the family of cyclodextrin adjuvants described in U.S. Pat. Nos. 6,610,310 and 6,165,995. Typically, SL-CD is formulated in a mixture with a metabolizable oil such as one or more unsaturated terpene hydrocarbons, for example, squalane and preferably with a non-ionic surfactant, such as polyoxyethylene sorbitan monooleate.

The term "SP-Oil" refers to an adjuvant that is an oil emulsion comprising: 1% to 3% vol/vol of polyoxyethylene-polyoxypropylene block copolymer; 2% to 6% vol/vol of squalane; 0.1% to 0.5% vol/vol of polyoxyethylene sorbitan monooleate; and a buffered salt solution.

The terms "vaccine" or "vaccine composition", which are used interchangeably, refer to pharmaceutical compositions comprising at least one immunogenic composition that induces an immune response in an animal. A vaccine or vaccine composition may protect the animal from disease or possible death due to an infection, and may or may not include one or more additional components that enhance the immunological activity of the active component. A vaccine or vaccine composition may additionally comprise further components typical to pharmaceutical compositions. A vaccine or vaccine composition may additionally comprise further components typical to vaccines or vaccine compositions, including, for example, an adjuvant or an immunomodulator. The immunogenically active component of a vaccine may comprise complete live organisms in either their original form, or as attenuated organisms in a modified live vaccine, or organisms inactivated by appropriate methods in a killed or inactivated vaccine, or subunit vaccines comprising one or more immunogenic components of the virus, or genetically engineered, mutated or cloned vaccines prepared by methods known to those skilled in the art. A vaccine or vaccine composition may comprise one or simultaneously more than one of the elements described above.

As used herein, "virulent" refers to the ability of a *Mycoplasma hyopneumoniae* strain to cause disease associated with *Mycoplasma hyopneumoniae* infection. Virulence can be evaluated by observing disease progression in the animal. An example of a "virulent" strain of *Mycoplasma hyopneumoniae* is that exemplified by the challenge strain of *Mycoplasma hyopneumoniae*, as described and used in the present invention. Other virulent strains of *Mycoplasma hyopneumoniae* are available from the American Type Culture Collection (ATCC), designated as Strain No. 25617 or 25095. The term "avirulent" refers to strains of *Mycoplasma hyopneumoniae* that are lacking in virulence. That is, avirulent strains, isolates, or constructs are non-pathogenic and are incapable of causing disease. As used herein the term "avirulent" is used synonymously with the term "non-virulent." Exemplified herein are compositions employing the *M. hyopneumoniae* avirulent live culture strain J (FCX3-Line 1, which is available from the American Type Culture Collection (ATCC) as Strain No. 27715). Another "avirulent" strain that is also available from the ATCC is designated as Strain No. 25934. The J strain designated as ATCC accession number 27715 was cloned from the parental J strain designated as ATCC accession number 25934, as described in the ATCC catalogue.

General Description

The present disclosure is based upon the discovery that one or two-dose regimens of a *Mycoplasma hyopneumoniae* composition, including an immunogenic composition or a vaccine composition, using one or more live avirulent *Mycoplasma hyopneumoniae*, such as, for example, strain J (FCX3-Line 1; ATCC Accession No. 27715) and one or more adjuvant, typically a biologically-acceptable adjuvant, are effective in protecting against and/or preventing or ameliorating disease associated with virulent *Mycoplasma hyopneumoniae* infection.

In one embodiment, other live avirulent strains of *Mycoplasma hyopneumoniae*, including, but not limited to, J strains, whose genome comprises a nucleic acid sequence having at least about 90% homology, or at least about 95% homology, or at least about 99% homology, with a reference J strain, are contemplated for use in the compositions and methods of the present invention.

In one embodiment, other live avirulent strains of *Mycoplasma hyopneumoniae*, including, but not limited to, J strains, which have at least about 70% polymorphic identity, or at least about 85% polymorphic identity, or at least about 95% polymorphic identity, to that of a reference J strain, are contemplated for use in the compositions and methods of the present invention.

The reference J strain may be selected from the *Mycoplasma hyopneumoniae* strains designated as ATCC accession number 25934 or 27715.

In one embodiment, the live avirulent J strain used in the compositions and methods of the present invention is a J strain designated as ATCC accession number 25934 or 27715.

In one embodiment, the live avirulent J strain used in the compositions and methods of the present invention is a J strain designated as ATCC accession number 27715.

It is also disclosed herein that compositions, including vaccine compositions, which employ one or more live avirulent *Mycoplasma hyopneumoniae* strain in further combination with Porcine Circovirus Type 1-Type 2 chimera modified live vaccine (cPCV1-2) (See U.S. Patent Publication number 2003/0170270 and number 2004/0253270) are also effective in protecting against and/or preventing or ameliorating disease associated with virulent *Mycoplasma hyopneumoniae* infection and/or virulent Porcine Circovirus infection.

In certain embodiments, the compositions of the invention further comprise one or more live bacteria, bacterin and/or one or more purified toxoid selected from the group consisting of *Haemophilus parasuis, Pasteurella multocida, Streptococcus suis, Actinobacillus pleuropneumoniae, Bordetella bronchiseptica, Salmonella choleraesuis, Erysipelothrix rhusiopathiae*, and leptospira bacteria.

In certain embodiments, the compositions of the invention further comprise one or more viral antigen selected from the group consisting of a swine influenza virus (SIV) antigen, a porcine reproductive and respiratory syndrome virus (PRRSV) antigen, raccoon poxvirus expressing PRRS or other antigens, TGEV expressing PRRS or other antigens, and a porcine circovirus (PCV) antigen.

Within certain embodiments, the present disclosure is described hereinafter with reference to protection against infection with a lung homogenate designated as LI-34 containing virulent *Mycoplasma hyopneumoniae* strain 11 (See J. Clin. Microbiol. 1999 March; 37(3):620-7. It is, however, contemplated that the compositions disclosed herein will be effective in protecting against and/or preventing or ameliorating disease or at least one symptom associated with the disease that are associated with a wide range of virulent *Mycoplasma hyopneumoniae* infections. Numerous virulent *Mycoplasma hyopneumoniae* isolates are known in the art and are available from various sources including the American Type Culture Collection, 12301 Parklawn Drive, Rockville, Md. 20852. Examples of these virulent strains include, but are not limited to, ATCC accession numbers 25095, 27714 and 25617.

Compositions, in particular immunogenic compositions or vaccine compositions, of the present disclosure may be prepared from lyophilized or freshly harvested cultures of live avirulent *Mycoplasma hyopneumoniae* by one or more methodology that is readily available in the art. Exemplified herein are compositions comprising the live avirulent *M. hyopneumoniae* strain J (FCX3-line 1), which is available as ATCC Number 27715 (a filtered and cloned 3 times isolate of ATCC Number 25934).

Live avirulent *Mycoplasma hyopneumoniae* may be cultured by the methodology described in U.S. Pat. Nos. 5,338,543 and 5,565,205, each of which is incorporated in its entirety herein. More specifically, *Mycoplasma hyopneumoniae* may be propagated in culture medium such as PPLO (Pleuropneumonia-like organism) complete medium (Difco; Becton Dickinson and Company, San Jose, Calif.). Growth of the organism is monitored by standard techniques such as determining color changing units (CCU), and harvested when a sufficiently high titer has been achieved. The stocks may be further concentrated or lyophilized by conventional methods before inclusion in the composition formulations. Other methods, such as those described in Thomas et al. *Agri-Practice* 7(5):26-30, may also be employed.

The conditions under which an isolate of *Mycoplasma hyopneumoniae* is grown may vary depending upon the precise composition of the medium and the specific isolate being grown. *Mycoplasma hyopneumoniae* isolates are typically grown from about 48 hours to about 144 hours, measured from the time of incubation to the time of harvest.

Depending upon the precise composition to be formulated, *Mycoplasma hyopneumoniae* may be concentrated by, for example, ultracentrifugation or ultrafiltration. The concentrated *Mycoplasma hyopneumoniae* may be recovered by methodology known in the art and may be mixed with a suitable physiologically acceptable carrier—typically an aqueous media such as, for example, saline, phosphate-buffered saline (PBS), minimal essential media (MEM), or MEM with HEPES buffer. It may then be further combined with an appropriate adjuvant to provide the desired concentration on a volume per volume basis (v/v). Compositions may further comprise one or more chelator, such as EDTA, typically at a concentration of about 0.05% to about 0.20% (w/v). Alternatively, the *Mycoplasma hyopneumoniae* strain to be used in the immunogenic or vaccine compositions may be concentrated as described above, or lyophilized and resuspended in an appropriate adjuvant at the desired concentration on a weight per volume (w/v) basis.

As indicated above, compositions, including immunogenic compositions or vaccine compositions, of the present disclosure generally comprise a live avirulent strain of *Mycoplasma hyopneumoniae* in combination with one or more adjuvant, typically a biologically acceptable adjuvant.

For one-dose administration, compositions may contain an amount of live avirulent *Mycoplasma pneunomoniae* corresponding to about $1 \times 10^8$ to about $3 \times 10^{11}$ MHDCE/ml. Alternatively, compositions may contain an amount of live avirulent *Mycoplasma pneunomoniae* corresponding to about $1 \times 10^9$ to about $3 \times 10^9$ MHDCE/ml. Compositions are formulated such that each administration dose will be between about one (1) ml and about five (5) ml, or between about two (2) ml, per animal for administration intramuscularly, subcutaneously, or intraperitoneally and between about one (1) and about ten (10) ml, or between about two (2) and about five (5) ml, for administration orally or intranasally.

For two-dose administration, compositions typically contain an amount of live avirulent *Mycoplasma pneumomoniae* of about $1 \times 10^8$ to about $3 \times 10^{11}$ MHDCE/ml, more typically about $1 \times 10^9$ to about $3 \times 10^9$ MHDCE/ml. In certain embodiments for two dose administration, compositions may contain an amount of live avirulent *Mycoplasma pneumomoniae* containing about $10^3$ CFU/ML TO $10^{11}$ CFU/ML. Compositions are formulated such that each administration dose will be between about one (1) ml and about five (5) ml, preferably about two (2) ml per animal for administration intramuscularly, subcutaneously, or intraperitoneally and between about one (1) and about ten (10) ml, typically between about two (2) and about five (5) ml for administration orally or intranasally.

The adjuvant mixture for use in the immunogenic compositions and vaccine compositions of the present disclosure enhances the immune response by stimulating cell mediated and/or local (secretory IgA) immune responses. The biologically acceptable adjuvant may, for example, be one or more adjuvant selected from the group consisting of SP-Oil, SL-CD, an acrylic acid polymer (such as Carbopol), and a mixture of a metabolizable oil such as one or more unsaturated terpene hydrocarbon(s), for example squalene or squalane, and a polyoxyethylene-polypropylene block copolymer such as Pluronic®. Adjuvants may be further selected from cytokines, such as IL-12 and IL-18; aluminum hydroxide; ethylene maleic acid copolymer; DEAE dextran; mycobacteria cell wall derived adjuvant; and the like.

The concentration of adjuvant employed in the compositions described herein will depend upon the nature of the adjuvant. Adjuvants are typically present in the compositions described herein at a final concentration of about 1-50% and more typically at a final concentration of about 10%, 15%, 20%, 25%, or 30%. The concentration of the antigen in the adjuvant may be prepared on a weight per volume basis (w/v) or on a volume per volume (v/v) basis. For example, the antigen to be delivered in the compositions of the invention may be prepared in a lyophilized form, followed by reconstitution in the adjuvant directly to result in the specified concentrations on a weight per volume basis. Alternatively, the antigen may first be reconstituted in an appropriate diluent (for example, a buffer) to which is then added an adjuvant in a volume sufficient to result in the final desired concentration of both antigen and adjuvant on a volume per volume basis, as described above.

In certain embodiments, an adjuvant may be administered with the antigen/immunogen as a single composition, or can be administered before, concurrent with, or after administration of the antigen/immunogen.

The choice of the adjuvant depends on the stability of the antigen/immunogen containing the adjuvant, the route of administration, the dosing schedule, the efficacy of the adjuvant for the species being vaccinated and must also be one approved for use in animals or humans by the pertinent regulatory bodies.

In compositions comprising SP-Oil, the adjuvant is typically present at between about 1% and about 25% (v/v), more typically between about 5% and about 15% (v/v) such as, for example, at about 10% (v/v); in compositions comprising an acrylic acid polymer and a mixture of a metabolizable oil that comprises one or more terpene hydrocarbon(s) and a polyoxyethylene-polypropylene block copolymer, the ratio of acrylic acid polymer to metabolizable oil/polyoxyethylene-polypropylene block copolymer mixture is typically in a ratio of between about 1:25 and about 1:50. A metabolizable oil, a polyoxyethylene-polypropylene block copolymer, and an acrylic acid polymer may be employed in the form of an oil in water emulsion wherein acrylic acid polymers are typically employed at a concentration of between about 0.5 g/l and about 10 g/l; metabolizable oils are typically employed at a concentration of between about 2 ml/l and about 6 ml/l; and polyoxyethylene-propylene block copolymers are typically employed at a concentration of between about 1 ml/l and about 3 ml/l.

Exemplary suitable adjuvant mixtures include, but are not limited to, mixtures of one or more acrylic acid polymer(s) with a mixture of metabolizable oil, for example an unsaturated terpene hydrocarbon or a hydrogenation product thereof, preferably squalane (2,3,10,15,19,23-hexamethyltetracosane) or squalene, and a polyoxyethylene-polyoxypropylene block copolymer. Such an acrylic acid polymer may be a homopolymer or a copolymer.

Acrylic acid polymers are typically carbomers. Carbomers are commercially available under the trade name Carbopol and are described, for example, in U.S. Pat. Nos. 2,909,462 and 3,790,665, each of which is incorporated herein by reference.

The polyoxyethylene-polyoxypropylene block copolymers are surfactants, typically liquid surfactants, which aid in suspending solid and liquid components. Surfactants are commercially available as polymers under the trade name Pluronic®. The surfactant poloxamer 401 is commercially available under the trade name Pluronic® L121.

The adjuvant mixture may comprise a metabolizable oil, an acrylic acid polymer and a polyoxyethylene-polyoxypropylene block copolymer formulated as an emulsion in an aqueous medium. Within certain embodiments, the adjuvant mixture may include a metabolizable oil and polyoxyethylene-polyoxypropylene block copolymer such as a mixture of squalane and Pluronic® L121 (poloxamer 401) which may be present in an amount of between about 50 ml/l and about 100 ml/l and the carboxymethylene polymer may be Carbopol 934P (Carbamer 934P), which may be present in amount of about 2 ml/l.

Preferred acrylic acid polymers are those marketed by B. F Goodrich as Carbopol 934 P NF and 941 NF, which are polymers of acrylic acid cross-linked with polyallylsucrose and which have the chemical formula $(CH_2CHOOOH)_n$. These polymers form aqueous gels which suitably formulate with aqueous carriers. Polyoxyethylene-polypropylene block copolymers may be the nonionic surfactants marketed by BASF as Pluronic® L121, L61, L81 or L101.

Within certain embodiments, compositions disclosed herein may employ, in further combination, one or more other live bacteria, bacterin, toxoid, and/or viral antigen. Thus, within certain aspects of these embodiments, the adjuvanted live avirulent M. hyopneumoniae composition may comprise an immunizing amount of a live avirulent Mycoplasma hyopneumoniae and one or more biologically acceptable adjuvant in further combination with (a) one or more live bacteria such as, for example, Haemophilus parasuis, Pasteurella multocida, Streptococcus suis, Actinobacillus pleuropneumoniae, Bordetella bronchiseptica, Salmonella choleraesuis, Erysipelothrix rhusiopathiae, and leptospira bacteria; (b) one or more bacterin; (c) one or more purified toxoid from one or more pathogens such as, for example, Haemophilus parasuis, Pasteurella multocida, Streptococcus suis, Actinobacillus pleuropneumoniae, Bordetella bronchiseptica, Salmonella choleraesuis, Erysipelothrix rhusiopathiae, and leptospira bacteria; and/or (d) one or more viral antigen wherein the virus is selected from the group consisting of swine influenza virus (SIV; such as SIV strains H1N1, H1N2, and H3N2), porcine reproductive and respiratory syndrome virus (PRRSV), raccoon poxvirus expressing PRRS and/or other antigens, TGEV expressing PRRS and/or other antigens, and porcine circovirus (PCV). Exemplified herein are compositions, including vaccine compositions, which employ one or more live avirulent Mycoplasma hyopneumoniae strain in further combination with porcine circovirus Type 1-Type 2 chimera modified live vaccine (cPCV1-2) (See U.S. Patent Publications 2003/0170270 and 2004/0253270).

Within these or alternative embodiments, compositions, including vaccine compositions, may additionally or optionally include a preservative such as, for example, thimerosol and/or EDTA. See, also, U.S. Patent Publication Nos. 2002/0131980 and 2003/0017171, each of which is herein incorporated by reference in its entirety.

The concentration of such other live bacteria, bacterin, toxoid, and/or viral antigen employed in the compositions described herein will depend upon the nature of the bacterin, toxoid, and/or viral antigen and are typically present in the compositions described herein at a final concentration of between about $0.5 \times 10^5$ to $0.5 \times 10^{10}$ per ml. Alternatively, the bacteria are present in a final concentration of between about $0.5 \times 10^6$ to $0.5 \times 10^9$ per ml or between about $0.5 \times 10^7$ to $0.5 \times 10^8$ per ml.

Compositions of the present disclosure will find utility in methods for protecting an animal against disease caused by Mycoplasma hyopneumoniae and/or for preventing or ameliorating an outbreak of such disease among animal populations by administration an adjuvanted live avirulent Mycoplasma hyopneumoniae composition as described herein. Compositions described herein may also be advantageously employed in methods for enhancing in an animal an immune response, such as a cell-mediated and/or humoral immune response, to Mycoplasma hyopneumoniae. Such methods comprise the steps of administering to an animal, typically swine, in one or two doses, a composition comprising one or more adjuvanted live avirulent Mycoplasma hyopneumoniae strain. Depending upon the precise application contemplated, compositions may be administered intramuscularly, subcutaneously, orally, by aerosol, or intranasally.

According to the methods of the present disclosure, a desirable dosage regimen involves administration of one or more doses of desired vaccine composition to the pig. Typically, where two doses are administered to the animal, the doses are administered between about one (1) week apart and about four (4) weeks apart, more typically between about two (2) weeks apart and about three (3) weeks apart.

EXAMPLES

The present disclosure will be better understood by reference to the following non-limiting examples:

Example 1

Preparation of an M. Hyopneumoniae Avirulent Adjuvanted Live Vaccine

This Example discloses the preparation of an exemplary adjuvanted live avirulent M. hyopneumoniae composition according to the present disclosure.

Mycoplasma hyopneumoniae may be obtained from any number of readily available sources. In one embodiment described herein, M. hyopneumoniae avirulent live culture strain J (FCX3-Line 1), was obtained from the American Type Culture Collection (ATCC; Manassas, Va.) as ATCC Strain No. 27715. Any other avirulent strain of M. hyopneumoniae may be used for preparation of the compositions, such as, for example, the parent J strain designated as ATCC accession number 25934. In certain other embodiments, it is envisioned that any live virulent strain of Mycoplasma pneumoniae, may be modulated, attenuated or mutated until the culture is established to be avirulent, as determined by in vitro or in vivo testing, using procedures known to those skilled in the art. The full genomic sequence of the ATCC 25934 J strain has been published by Vasconcelos et al (J. Bacteriol. (2005), 187(16): 5568-5577) and has been assigned GenBank accession number AE017243. Several of the sequences associated with ATCC strain 25934 may be found in PubMed and have GenBank accession numbers AY737012 (16S ribosomal RNA gene), AY512905 (adhesin gene, AF013714 (prolipoprotein p65 gene), U02538 (23S rRNA gene) and U02537 multidrug resistance protein homolog genes).

Each vaccine composition for the bactericidal assay was prepared from one lyophilized vial of a M. hyopneumoniae culture rehydrated with 20 ml of normal saline. Vaccine compositions included a combination of 5 ml of the rehydrated culture and adjuvant sufficient to acquire the specified adjuvant concentration in a final volume of 10 ml. A control composition was also prepared by combining 5 ml of rehydrated culture with 5 ml of normal saline. All compositions were mixed for 5 minutes prior to sampling. Samples were taken from all compositions at 5 minutes (0 hour), 3 hours, and 7 hours after blending. The viability of each vaccine was determined by Colony Forming Units (CFU) at each sampling point (see Table 1).

TABLE 1

| | CFU/ml | | | MPN/ml | | |
|---|---|---|---|---|---|---|
| Adjuvant | 0 hour | 3 hour | 7 hour | 0 hour | 3 hour | 7 hour |
| 30% SL-CD | 1.44E+07 | 0 | 0 | 1.15E+07 | 0 | 0 |
| 10% SL-CD | 1.48E+07 | 6.40E+05 | 5.2E+03 | 2.87E+07 | 8.42E+05 | 0.00E+00 |
| Control | 8.30E+07 | 1.06E+08 | 9.00E+07 | 3.62E+07 | 6.22E+07 | 3.62E+07 |
| 5% SP-Oil | 9.46E+07 | 7.60E+07 | 2.55E+07 | 4.67E+07 | 9.40E+07 | 6.22E+06 |
| 5% SP-Oil/0.2% | 1.50E+08 | 5.61E+07 | 4.53E+07 | 4.27E+08 | 7.74E+07 | 2.84E+06 |
| Control | 2.17E+08 | 1.41E+08 | 9.86E+07 | 1.91E+08 | 8.42E+07 | 4.67E+07 |
| 10% SP oil | 1.09E+07 | 1.07E+07 | 7.13E+06 | 3.40E+06 | 7.74E+06 | 3.62E+06 |
| Control | 3.50E+07 | 4.75E+07 | 7.20E+07 | 1.03E+07 | 8.42E+07 | 3.14E+07 |
| 10% Sp-oil + 0.2% carbopol | 5.20E+07 | 1.30E+07 | 8.13E+06 | 5.50E+07 | 1.91E+07 | 2.26E+06 |
| 0.2% carbopol | 6.80E+07 | 6.67E+07 | 6.60E+07 | 1.63E+08 | 1.38E+08 | 4.45E+07 |
| control | 2.90E+07 | no test | 5.54E+07 | 1.23E+08 | No test | 1.38E+07 |

The average viability of the stock culture was determined by averaging all the control viabilities at 0 hour, average $9.09\times10^7$ CFU/ml. In comparison, the most-probable number (MPN) was determined for the stock cultures resulting in $1.85\times10^8$ MPN/ml. Vaccine blending and vaccination typically takes less than 3 hours; therefore when looking at the bactericidal effect of adjuvants, the 3 hour time point is the most important. The trend for SP-Oil at 5% and 10% at the 3-hour sampling compared to the control is a 2-fold difference and 4-fold difference, respectively.

Vaccine A was prepared by rehydrating vials of lyophilized culture with diluent containing 10% (v/v) SP-Oil final concentration. The placebo vaccine was sterile normal saline.

Example 2

In vivo Efficacy of *M. hyopneumoniae* Avirulent Adjuvanted Live Vaccines in Pigs This Example demonstrates the in vivo efficacy of exemplary adjuvanted live avirulent *M. hyopneumoniae* vaccine compositions.

A total of 30, four to six week-old pigs were acquired from Fort Dodge Animal Health's SPF herd in Charles City, Iowa. Pigs were maintained on feed without antibiotics or growth promotants and given water and food ad libitum. Animals receiving vaccine compositions and control compositions were housed in different rooms and all pigs were maintained under similar conditions during vaccination, monitoring, and challenge periods.

The 30 pigs were randomly assigned into three (3) groups as follows: One (1) group received a vaccine composition, one (1) group received a placebo, and one (1) group served as an environmental control. Pigs were grouped as shown in Table 2.

TABLE 2

| Group | Total# of | Vaccine | # Pigs |
|---|---|---|---|
| 1 | 13 | A | 13 |
| 2 | 12 | placebo | 12 |
| 3 | 5 | N/A | N/A |

Four to six week-old pigs were vaccinated intramuscularly with a 2 ml dose of the appropriate vaccine. Group 1 was administered vaccine A, group 2 was administered the placebo. Pigs from group 3 were not vaccinated or challenged and served as environmental controls. Pigs in group 1 were vaccinated twice, two weeks apart. Two weeks after the second vaccination, all pigs in groups 1 and 2 were challenged with a lung homogenate (LI-34) containing a virulent strain of *M. hyopneumoniae* Strain 11 (J. Clin. Microbiol., 1999 March; 37(3):620-7) Four weeks after challenge, all pigs in groups 1-3 were necropsied and lung lesions were evaluated.

Preparation of Lung Homogenate (LI-34) for *M. hyopneumoniae* Challenge Strain

Seven cross-bred pigs were procured from Spring Prairie Colony Farms (Genetipork) and were inoculated intratracheally with 10 ml of a 1:30 dilution of a 10% crude lung homogenate (LI31) of *M. hyopneumoniae* strain 11. The LI31 crude lung homogenate had been produced by passaging lung homogenate containing *M. hyopneumoniae* in specific pathogen free pigs and harvesting the resulting pneumonic lungs at early mid-stage of the disease. The lung homogenates were stored at −70° C. until needed.

Serum was collected upon arrival and at necropsy from all pigs and was evaluated at the ISU Veterinary Diagnostic Laboratory (ISU-VDL) for evidence of antibodies to TGE (PRCV), SW and PRV. In addition, ELISA's for PRRSV and *M. hyopneumaniae* antibodies were performed and all samples were negative for all of the above respiratory pathogens.

All pigs were necropsied. Pentobarbital was used to induce deep anesthesia of pigs prior to exsanguination. The ventral chest wall was opened and areas of pneumonic lesions typical of *M. hyopneumoniae* were removed aseptically and placed individually in sterile containers.

A small portion of each lung was ground and checked for purity on blood agar plates, beef heart infusion broth, and Friis media. Tube dilutions were performed in Friis media to titrate out the *M. hyopneumoniae*. Tie remaining lung pieces were frozen in 50 ml centrifuge tubes at −70° C. until the results of the bacteriology and mycoplasma isolation were known. Lung lobes from 3 of the 7 pigs were used to produce the *M. hyopneumoniae* lung inoculum.

Lobe chunks were thawed from pigs #329, 331, and 332 and ground in Friis media containing no antibiotics. Purity of lung inoculum was confirmed by culture on beef heart infusion, blood agar and Friis media. Only micrococci consistent with environmental contamination were found on one plate. The lung inoculum was titrated for *M. hyopneumoniae* levels and found to contain approximately $10^7$ CCU/ml. An aliquot was submitted to ISU-VDL for virus isolation assays for SN, EMS, enterovirus, HEV, PRCV, PRRSV, Pseudorabies, TGE, parvovirus, and rotavirus. The results of all assays were negative. Final volume of ground lung inoculum (labeled LI 34) was 1780 ml from 178.1 grams of lung tissue. This was aliquoted into 100×5 ml and 110×10 ml volumes.

In the second phase of the study, 9 pigs were used in the determination of the concentration of lung inoculum required to induce an average of 8% pneumonic-lung lesions in a minimum of 80% of the pigs. All pigs were challenged with the L134 *M. hyopneumoniae* strain 11 intratracheally on as previously described. Challenge dilutions included 1:30, 1:100, and 1:500.

The pigs were necropsied. Pentobarbital was used to induce deep anesthesia prior to exsanguination. The lungs were removed and lung lesions sketched on standard lung diaphrams. Serum was collected from all pigs and was assayed by ELISA for antibodies to *M. hyopneumoniae*. All pigs were either low positive or seronegative for *M. hyopneumoniae* suggesting no previous exposure to *M. hyopneumoniae* prior to arrival. Tracheal swabs were collected aseptically from all pigs. *Pasteurella multocida* and *Haemophilus parasuis* were isolated from 4 and 3 pigs respectively. *M. hyopneumoniae* was isolated from all challenged pigs. Lung sketches were evaluated with a Zeiss Image analysis system to determine the percentage of pneumonic lung lesions.

Conclusions

The challenge of the pigs was successful and a dilution of 1:100 would be the optimal dilution to use. The average percentage of pneumonia induced was 10.17+/−6.6, which is higher than normal, however this may be attributed to the presence of *Pasteurella multocida* and/or *parasuis* in the pigs. In addition, 100% of the pigs inoculated with the challenge inoculum had significant lung lesions. Overall, these results are fairly typical of what we observe in our studies of *M. hyopneumoniae*, in that if there are other pathogens present, there is an increase in pneumonia. This may be due to the interaction between the pathogens and the immune system. We produced 1,600 ml of *M. hyopneumoniae* lung inoculum for use in experimental challenge experiments. The inoculum will produce at least 8% or higher pneumonic lung lesions in a minimum of 80% of inoculated pigs when used at a 1:100 dilution intratracheally.

The vaccine was titrated prior to the day of vaccination and bactericidal assays were conducted to determine the appropriate adjuvant systems to be used (see Example 1). From these data, 10% SP-Oil adjuvant system was chosen for further study. The average viability per vial of stock culture was $3.64\times10^{9}$ CFU/Bottle.

On the day of the first administration, vaccine compositions were prepared as follows: Vaccine A—each of three vials of avirulent *M. hyopneumoniae* lyophilized culture was rehydrated with 10 ml of 10% SP-Oil diluent. The three vials of vaccine composition for each diluent type were pooled and allowed to mix for 20 minutes on a stir plate with stir bar. The placebo was normal saline aliquoted into a sterile bottle for administration. The compositions remained on ice during the course of vaccination for 2 hours.

On the day of the second administration, vaccine compositions were prepared as follows: Vaccine A—each of three vials of avirulent *M. hyopneumoniae* lyophilized culture was rehydrated with 10 ml of 10% SP-Oil Diluent. The three vials of rehydrated culture for each diluent type were pooled and allowed to mix for 20 minutes on a stir plate with stir bar. The placebo was normal saline aliquoted into a sterile bottle for administration. The compositions remained on ice during the course of vaccination for 2 hours.

The concentration of viable *M. hyopneumoniae* in each composition was determined before and after administration. Viability was evaluated by determining Colony Forming Units (CFU/ml). A vial of lyophilized stock culture was rehydrated with 10 ml of normal saline, allowed to mix for 20 minutes, and served as a control for the viability assay. Since the first control viability was lower than the test vaccine viability, during the second administration, two vials were rehydrated and pooled to serve as the control (see Table 3 for test vaccine viabilities and control viabilities).

TABLE 3

| Vaccine | First Vaccination CFU/mL | Second Vaccination CFU/mL |
|---|---|---|
| Group 1: Adjuvant 10% SP-Oil | 2.79E+08 | 2.27E+08 |
| Viability Control | 1.29E+08 | 2.69E+08 |

All pigs were observed daily for temperatures and clinical symptoms starting two days prior to each administration and continued for seven days after each administration. Pigs were observed for clinical symptoms, which included, but were not limited to, coughing, sneezing, nasal discharge, depression, inappetance, and labored breathing.

Fourteen days after the second administration, pigs in group 1 were challenged trans-tracheally with a virulent strain of *M. hyopneumoniae.*

On the day of challenge, a virulent *M. hyopneumoniae* challenge stock of frozen (−70° C.) lung homogenate (LI-34), was thawed rapidly under warm water and diluted (1:100 dilution) with. Pigs were sedated with a mixture of Xylazine-Ketamine-Telazol™ consisting of 50 mg/ml Xylazine, 50 mg/ml Ketamine, and 100 mg/ml Telazol. Each pig was given 10 ml of the challenge material trans-tracheally. To ensure needle placement, air was drawn into the syringe prior to administration of the challenge material. All pigs were observed daily for clinical symptoms post-challenge.

Pigs were bled for serum on days 0, 14, 28, and 56. Serological response of the pigs to *M. hyopneumoniae* challenge was determined by ELISA. Four weeks after challenge, all pigs from groups 1-3 were euthanized and lungs were removed. Test groups were blinded and scored for gross lung lesions. Atypical *M. hyopneumoniae* lesions were formalin fixed for subsequent histopathological evaluation. Swab samples from affected lung were collected for bacterial isolation.

The average lung lesion score for pigs in group 1 (5.9%) was approximately 50% less than the placebo group (14.8%). When the statistical analysis was adjusted for litter, the mitigated fraction for group 1 was 69.2% reduction in severity of lung lesions when compared to controls. These data are summarized in Table 4. All of the pigs were sero-negative on the day of first administration indicating that the pigs were susceptible to *M. hyopneumoniae* infection. With the exception of one (1) pig in the SP-Oil group, pigs did not sero-convert after the first vaccination. All pigs receiving the SP-Oil adjuvanted vaccine composition developed an antibody response after the second shot. Serological response demonstrates that an immune response to *M. hyopneumoniae* was elicited. (See Table 9. for serology results)

TABLE 4

| Vaccine | Description | Mitigated Fraction Reduction in Lesions Compared to Control | Mitigated Fraction Reduction Lower Confidence Level |
|---|---|---|---|
| Vaccine A | Avirulent *M. hyopneumoniae* live with 10% SP-Oil | 69.2 | 40.2 |
| Control | Placebo | NA | NA |

The statistical analysis of the data must meet the criteria for the mitigated fraction (<50% with lower confidence level >30%) for reduction in lung lesions for a vaccine to be considered efficacious for M. hyopneumoniae. In total, these data demonstrate that a live avirulent adjuvanted M. hyopneumoniae may be advantageously employed for eliciting a protective immune response when administered in vivo to an animal.

While the invention has been described in each of its various embodiments, it is expected that certain modifications thereto may be undertaken and effected by the person skilled in the art without departing from the true spirit and scope of the invention, as set forth in the previous description and as further embodied in the following claims. The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description. All patents and patent applications cited herein are hereby incorporated herein by reference in their entireties.

Example 3

Preliminary Immunogenicity Study of the
*Mycoplasma hyopneumoniae* Fraction of
*Mycoplasma hyopneumoniae* Live Avirulent
Strain-Porcine Circovirus Type 1-Type 2 Chimera
Modified Live Combination Vaccine in 3 to 4 Week
Old Pigs Combination Vaccine in 3-4 Week Old Pigs This Example discloses the efficacy of a combination vaccine comprising an adjuvanted live avirulent *Mycoplasma hyopneumoniae* J (FCX3-line1) strain and a Porcine Circovirus (PCV) Type 1-Type 2 Chimera live vaccine (cPCV1-2; see U.S. Pat. Nos. 7,279,166 and 7,276,353) when administered intramuscularly (IM) or intranasally (IN) in 3-4 week old pigs. This combination vaccine (PCV/MH) is suitable for use for the vaccination of healthy swine as an aid in the prevention and/or to reduce the severity of disease caused by M. hyopneumoniae and Porcine Circovirus.

The targeted test vaccine should contain about 4.0 $Log_{10}$ $FAID_{50}$/dose of cPCV1-2 modified live virus and $4 \times 10^8$ CFU/dose of M. hyopneumoniae J strain (see King et al, Journal of Comparative Medicine and Vet. Science, 29: 85-89 (1965) and U.S. Pat. No. 4,824,785 for the FAID method). The vaccine was adjuvanted to contain 10% (v/v) SP-Oil final concentration. The placebo vaccine was sterile Normal Saline.

A total of 66 3-4 week-old pigs were employed in this study. 16 pigs were administered 2 ml of PCV/MH live vaccine intramuscularly once and challenged (Group 1); 15 pigs were administered 2 ml of PCV/MH live vaccine intramuscularly twice (two weeks apart) and challenged (Group 2); 15 pigs were administered 2 ml (1 ml/nostril) of PCV/MH live vaccine intranasally twice (two weeks apart) and challenged (Group 3); 15 pigs were not administered the PCV/MH live vaccine and challenged (Group 4); and 5 pigs served as environmental controls (Group 5).

The vaccine used in the study disclosed herein was a combination of MH lyophilized live antigen (lot#1744-56) and diluent containing PCV (LotC108-56) live vaccine. On the day of vaccination, the lyophilized live MH cake was rehydrated with diluent containing PCV live virus (4.0 $Log_{10}FAID_{50}$/mL adjuvanted with 10% SP Oil). Final vaccine was assigned Lot# 2315-30. Viability for the MH fraction was determined before and after vaccination, $3.18 \times 10^8$ CFU/mL (before) and $1.65 \times 10^8$ CFU/mL (after), respectively. The PCV titer for the vaccine pre and post vaccination was 4.09 $Log_{10}$ $FAID_{50}$ and 3.7 $Log_{10}$ $FAID_{50}$, respectively. The vaccine for second vaccination was prepared as above and assigned Lot# 2315-32. Viability for the MH fraction was $1.24 \times 10^8$ CFU/mL and $1.5 \times 10^8$ CFU/mL pre and post vaccination respectively. The viability for the PCV fraction was 4.36 $Log_{10}$ $FAID_{50}$ and 3.83 $Log_{10}$ $FAID_{50}$, respectively.

The pigs were observed for 7 days following vaccination for any adverse reactions to the vaccine. Three pigs died during the post vaccination observation period due to non-MH or PCV related causes. A summary of the clinical observations from the post vaccination period is found in Table 5.

TABLE 5

| Group | # of pigs | Treatment | Route | Dosage | Observation after vaccination |
|---|---|---|---|---|---|
| 1 | 16 | Vaccination | IM | 1 dose | One pig was noted to have elevated temp (105.1-106.2° F.) for 7 consecutive days starting on fifteen days post first vaccination. Another pig was noted to have an elevated temp, inappetance and depression for 4 consecutive days starting 18 days post first vaccination. |
| 2 | 15 | Vaccination | IM | 2 doses | One pig died the day before second vaccination due to possible HPS or *S. suis* infection. Clinical signs of depression and thin were noted prior to vaccination. One pig had 3 consecutive days of elevated temp (105.0-106.7° F.) starting 5 days post first vaccination. |
| 3 | 15 | Vaccination | IN | 2 doses | Two days prior to second vaccination one pig died due to intestinal perforation. Two pigs had swollen joints and coughing for 8 consecutive days, which had originated prior to first vaccination. Two other pigs one day prior to second vaccination was noted to have swollen hocks for 7 |

TABLE 5-continued

| Group | # of pigs | Treatment | Route | Dosage | Observation after vaccination |
|---|---|---|---|---|---|
| | | | | | consecutive days in which one resulted in an abscess, the other healed. |
| 4 | 15 | Saline | IM | 2 doses | One pig was noted to have swollen hocks throughout the study noted prior to first vaccination. Another pig also had swollen hocks for several days during the study. One pig had two days of elevated temp. for two consecutive days 105.1° F. and 106.5° F. starting 6 days after second vaccination. |
| 5 | 5 | No Vaccination | NA | NA | Housed with group 4 pigs during vaccination. No adverse reactions noted. |

NA: Not applicable
IN: intranasal
IM: intramuscular

All pigs in Groups 1-4 were challenged with a virulent strain of *M. hyopneumoniae* (pig lung homogenate containing virulent MH (LI-34)). Pigs from Group 1 were challenged four weeks after first vaccination. Pigs in Groups 24 were challenged two weeks after second vaccination. At four weeks after challenge, all pigs in Groups 1-5 were necropsied and lung lesions were evaluated.

The vaccine was titrated prior to the day of vaccination. Lyophilized culture of avirulent *M. hyopneumoniae* was rehydrated on the day of vaccination. The concentration of *M. hyopneumoniae* organisms in the vaccine was approximately $2 \times 10^8$ CFU/ml. A sample of vaccine was retained and a viability assay performed before and after vaccination to confirm actual CFU/ml. The vaccine was held on ice during the course of vaccination.

All pigs were observed daily for temperatures and clinical signs starting two days prior to each vaccination continuing for seven days after each vaccination. Pigs were observed for clinical symptoms, which included, but were not limited to, coughing, sneezing, nasal discharge, depression, inappetance, and labored breathing. 14 days after the second vaccination, pigs in Groups 1-4 were challenged trans-tracheally with a virulent strain of *M. hyopneumoniae*.

On the day of challenge, the virulent *M. hyopneumoniae* challenge stock, a frozen (−70° C.) lung homogenate (LI-34) was thawed rapidly under warm water and diluted (1:100 dilution) using sterile *M. hyopneumoniae* growth medium. Pigs were sedated with a mixture of Xylazine-Ketamine-Telazol™ comprising 50 mg/ml Xylazine, 50 mg/ml Ketamine and 100 mg/ml Telazol. Each pig was given 10 ml of the challenge material transtracheally. To ensure needle placement, air was drawn into the syringe prior to administration of the challenge material.

All pigs were observed grossly for clinical signs after challenge. The observation was conducted daily for any abnormal clinical sign. Pigs were bled for serum (no more than 13 ml whole blood) on day 0, 14, 28, and 56 of the study. Serum was collected, but not evaluated. ELISA may be conducted to evaluate serological response of the pigs using the serum collected during the study period in the future.

Four weeks after challenge, all pigs from Groups 1-5 were euthanized and lungs were removed. Atypical *M. hyopneumoniae* lesions were formalin fixed and the samples were examined for histopathology. Swab samples from affected lung were collected for bacterial isolation. Pigs that died after challenge were necropsied and samples collected as described above. Vaccine efficacy was defined as a combined average lung lesion score of the vaccinates that was 50% less than the combined average lung lesion score of the controls.

On the day of necropsy all pigs were euthanized, lung lesions scored and swabbed for bacterial isolation. Bacteria isolated from the swabs consisted of the following: *Staphylococcus heamolyticus, Streptococcus suis* (P322), *Staphylococcus epidermis, A. pyogenes, aerococus* species, *S. uberis, Bordetella bronchiseptica* (P344) and Microbacterium. The statistical analysis for the Lung lesion scores is in Table 6.

TABLE 6

| Group | Protection ratio | MF litter adjusted | MF Lower confidence level | Litter adjusted percent lung lesion score | LCL lung lesion score | Standard deviation of lung lesion | Mean percentile for lesions |
|---|---|---|---|---|---|---|---|
| Vaccinate IM single dose | 1/15 | 52.9% | 19.6% | 6.30% | 3.86% | 4.41 | 0.37 |
| Vaccinate IM double dose | 3/15 | 63.8% | 33.8% | 5.03% | 2.39% | 4.59 | 0.31 |
| Vaccinate IN double dose | 0/14 | −8.6% | −51.8% | 12.86% | 8.59% | 7.38 | 0.65 |
| Control | 0/15 | NA | NA | 11.46% | 8.41% | 5.5 | 0.62 |

LCL = Lower Confidence Level
MF = Mitigated Fraction

The statistical analysis of the data met the criteria for the mitigated fraction (<50%, with LCL >30%) for reduction in lung lesions. This example demonstrates (a) the efficacy of the MH/PCV vaccine for the MH fraction with two 2 mL doses administered IM, at $3.18 \times 10^8$ CFU/mL and (b) the safety of the MH/PCV vaccine due to lack of clinical signs related to MH or PCV following vaccination.

Example 4

Immunogenicity Study of the *Mycoplasma hyopneumoniae* Fraction of *Mycoplasma hyopneumoniae* Live Avirulent Strain-Porcine Circovirus Type 1-Type 2 Chimera Modified Live Combination Vaccine in 3-4 Week Old Pigs This Example discloses an immunogenicity study which supports the results from the study presented in Example 3 and confirms the efficacy of the *M. hyopneumoniae* fraction of *Mycoplasma hyopneumoniae* live avirulent strain-Porcine Circovirus Type 1-Type 2 (cPCV1-2) chimera modified live vaccine combined vaccine (MH/PCV) when administered intramuscularly. The MH/PCV vaccine disclosed herein may be suitably employed for the vaccination of healthy swine as an aid in preventing and/or minimizing the severity of disease caused by *M. hyopneumoniae* and Porcine Circovirus.

The pigs used in the present study were sero-negative to *M. hyopneumoniae* as determined by ELISA.

A total of 79, three to four week-old pigs were randomized into four groups. 24 pigs, Group 1, were vaccinated with a single dose of the combination PCV/MH live vaccine. 24 pigs, Group 2, were vaccinated with the combination vaccine twice two weeks apart. 24 pigs, Group 3, were vaccinated with normal saline twice two weeks apart to serve as challenge controls. All vaccines were administered intramuscularly. Four pigs, Group 4, were neither vaccinated nor challenged and served as environmental controls.

The vaccine used in the study was a combination of MH lyophilized live antigen (Lot1744-66) and diluent containing PCV (cPCV1-2 LotC108-56) live vaccine. On the day of vaccination, the lyophilized live MH cake was rehydrated with diluent containing PCV live virus (3.5 $Log_{10}FAID_{50}$/mL adjuvanted with 10% SP Oil). Final vaccine was given Lot2315-40. Viability for the MH fraction was determined before and after vaccination, $2.09 \times 10^8$ CFU/mL and $1.56 \times 10^8$ CFU/mL respectively. The placebo vaccine was sterile normal saline.

The vaccine for second vaccination was prepared as above and given Lot# 2315-42. Viability for the MH fraction was $1.05 \times 10^8$ CFU/mL and $6.72 \times 10^7$ CFU/mL pre and post vaccination respectively. The viability for the PCV fraction diluent was 3.44 $Log_{10}$ $FAID_{50}$.

The vaccine was titrated prior to the day of vaccination. Lyophilized culture of avirulent *M. hyopneumoniae* was rehydrated on the day of vaccination. A sample of vaccine was retained and a viability assay performed before and after vaccination to determine CFU/ml. The vaccine remained on ice during the course of vaccination.

All pigs were observed daily for temperatures and clinical signs starting two days prior to each vaccination continuing for 7 days after each vaccination. Pigs were observed for clinical symptoms, which included, but were not limited to, coughing, sneezing, nasal discharge, depression, inappetance, and labored breathing.

The pigs were observed for 7 days following vaccination for any adverse reactions to the vaccine. Three pigs died during the post vaccination observation period due to non-MH or PCV related causes. A summary of the clinical observations from the post vaccination period is found in Table 7.

TABLE 7

| Group | # of pigs | Treatment | Dosage | Observation after vaccination |
|---|---|---|---|---|
| 1 | 24 | Vaccination | 1 dose | No adverse reactions noted due to vaccination |
| 2 | 24 | Vaccination | 2 doses | One pig died in this group due to intestinal perforation. On 5 days post first vaccination one pig had a temp of 105.5° F. and labor breathing noted for one day. |
| 3 | 24 | Saline vaccination | NA | On 6 days post first vaccination one pig was noted with labor breathing for a single day. |
| 4 | 4 | No Vaccination | NA | Housed with group 3 pigs during vaccination. No adverse reactions noted. |

NA: Not applicable

All pigs in Groups 1-3 were challenged with a virulent strain of *M. hyopneumoniae* at approximately 7 weeks of age. Pigs from Group 1 were challenged four weeks after first vaccination. Pigs in Groups 2 and 3 were challenged two weeks after second vaccination. The virulent *M. hyopneumoniae* challenge stock, a frozen (−70° C.) lung homogenate (LI-34) was thawed rapidly under warm water and diluted (1:100 dilution) using sterile *M. hyopneumoniae* growth medium. Pigs were sedated with a mixture of Xylazine-Ketamine-Telazol™ comprising 50 mg/ml Xylazine, 50 mg/ml Ketamine, and 100 mg/ml Telazol. Each pig was given 10 ml of the challenge material trans-tracheally.

Pigs were bled for serum on day 0, 14, 28, and 56 of the study. Serum samples collected from this study may be tested to evaluate animal serological response to *M. hyopneumoniae* and PCV2 using ELISA methods well known in the art. Serum samples collected from zero-days post vaccination (0DPV) and zero-days post challenge (0DPC) may be tested for antibodies to *M. hyopneumoniae*, Swine influenza (H1N1), and porcine reproductive and respiratory syndrome (PRRS) using commercially available ELISA test kits.

Four weeks (28 DPC) after challenge, all pigs from groups 1-4 were euthanized and lungs were removed. Lung lesion scores were recorded and typical *M. hyopneumoniae* lesions were formalin fixed. Samples were examined for histopathology. Swab samples from one *M. hyopneumoniae* affected lobe were collected for bacterial isolation for detection of secondary infections. In addition, bronchial alveolar lavage fluid was collected. The lungs were lavaged with phosphate buffered saline and the resulting fluid was aliquoted for testing by PCR.

For the evaluation of reduction in the severity of lung lesions, the estimator was the mitigated fraction (MF) statistic. The mitigated fraction was calculated as:

$$MF = \frac{2W_1 - n_c(1 + n_c + n_v)}{n_c n_v}$$

where:
w₁=Wilcoxon Rank sum statistic
$n_c$=number of subjects in the control group
$n_v$=number of subjects in the vaccinated group
The 95% confidence interval for the mitigated fraction was calculated.

For the claim of reduction in severity of lung lesions:
$H_O$: $M_v = M_c$
$H_A$: $M_v, M_c$ where:
$M_v$=Median of the lung lesion score in the vaccinated group
$M_c$=Median of the lung lesion score in the control group The frequency distribution of the continuous outcome variables was assessed using PROC UNIVARIATE, which performs parametric and nonparametric analysis of a sample from a single population. (SAS Institute Inc., Cary N.C.). Log transformations of the antibody titers were employed to meet the normality assumption required for parametric tests. Baseline evaluations to evaluate comparability of groups for litter and room will be made by chi-square. The severity of lung lesions was compared between each vaccinated group and the control group by Wilcoxon rank sum test (PROC NPAR1WAY with lung lesion score as the dependent variable and treatment included as an independent variable. PROC NPAR1WAY, which performs nonparametric tests for location and scale differences across a one-way classification; PROC NPAR1WAY also provides a standard analysis of variance on the raw data and statistics based on the empirical distribution function. (SAS Institute Inc., Cary N.C.).

All statistical analysis will be performed using the SAS system. In cases where transformation did not improve the distribution of the residuals for any transformed variables as determined by the W test for normality, non-parametric tests were employed as needed. The level of significance will be set at $p<0.05$.

On the day of necropsy all pigs were euthanized, lung lesions scored and swabbed for bacterial isolation. Bronchoalveolar lavages (BAL) were also collected. Bacteria isolated from the swabs consisted of the following: *Actinobacillus* species, *Moraxella osloensis*, *Streptococcus sanguinis*, *A. pyogenes* and *Bordetella bronchiseptica*. BAL samples were tested for MH by PCR methodology; two samples from environmental control group with lesions recorded and two samples with low lesion scores in the vaccinate and control group. BAL samples for both pigs from the environmental control group with lesions were negative and both pigs in with low lesion scores in the vaccinate group were positive. The statistical analysis for the lung lesion scores is in Table 8.

The statistical analysis of the data met the criteria for the mitigated fraction (<50%, with LCL >30%) for reduction in lung lesions. The vaccine is considered efficacious for the MH fraction with a 2 mL dose administered IM, either single dose or double dose, at $2.09 \times 10^8$ CFU/mL. In addition the vaccine is considered safe due to lack of clinical signs related to MH or PCV following vaccination.

TABLE 9

SEROLOGY RESULTS FOR EXAMPLE 2

| Pig ID | Group | ODPV1 | 0DPV2 | 0DPC | Necropsy | Lung score |
|---|---|---|---|---|---|---|
| 730 | 1 | <50 | 100 | 400 | 400 | 9.5 |
| 733 | 1 | <50 | <50 | 100 | >400 | 35.5 |
| 735 | 1 | <50 | <50 | 100 | 200 | 5.5 |
| 740 | 1 | <50 | <50 | 200 | 400 | 5.5 |
| 742 | 1 | <50 | <50 | 200 | 200 | 0.5 |
| 745 | 1 | <50 | <50 | 200 | 100 | 0.9 |
| 754 | 1 | <50 | <50 | 400 | 400 | 6.8 |
| 755 | 1 | <50 | <50 | 400 | >400 | 0.0 |
| 761 | 1 | <50 | <50 | 200 | 200 | 4.5 |
| 762 | 1 | <50 | <50 | >400 | 200 | 0.5 |
| 763 | 1 | <50 | <50 | 400 | 200 | 2.7 |
| 771 | 1 | <50 | <50 | >400 | >400 | 5.5 |
| 774 | 1 | <50 | <50 | >400 | >400 | 0.0 |
| 732 | 2 | <50 | <50 | <50 | <50 | 1.8 |
| 738 | 2 | <50 | <50 | <50 | <50 | 5.9 |
| 739 | 2 | <50 | <50 | <50 | 50 | 18.2 |
| 743 | 2 | <50 | <50 | <50 | 50 | 19.1 |
| 747 | 2 | <50 | <50 | <50 | 200 | 0.5 |
| 749 | 2 | <50 | <50 | <50 | 50 | 21.4 |
| 752 | 2 | <50 | <50 | <50 | <50 | 9.5 |
| 759 | 2 | <50 | <50 | <50 | <50 | 15.9 |
| 764 | 2 | <50 | <50 | <50 | <50 | 26.4 |
| 768 | 2 | <50 | <50 | <50 | <50 | 31.8 |
| 769 | 2 | <50 | <50 | <50 | <50 | 16.8 |
| 773 | 2 | <50 | <50 | <50 | <50 | 10.0 |
| 726 | 3 | <50 | <50 | <50 | <50 | 0.0 |
| 744 | 3 | <50 | <50 | <50 | <50 | 0.0 |
| 750 | 3 | <50 | <50 | <50 | <50 | 0.0 |
| 767 | 3 | <50 | <50 | <50 | <50 | 1.4 |
| 770 | 3 | <50 | <50 | <50 | <50 | 0.5 |

Group 1: SP Oil vaccine (vaccinated and challenged)
Group 2: Control/challenge (unvaccinated and challenged)
Group 3: Non-challenged control (unvaccinated and not challenged)
ODPV1 and ODPV2: The numbers indicate the highest dilution that was positive in the ELISA test after the first dose of vaccine (ODPV1) or after the second dose of vaccine (ODPV2).
ODPC: The numbers indicate the ELISA results Post Challenge. The higher number indicates seroconversion.
Lung Score: The number indicates the percent of lesions in the lungs of the animals. The higher number indicates a greater number of lung lesions due to a lack of protective immunity. The lower number indicates a healthier pig with fewer lesions due to induction of a protective immune response.

TABLE 8

| Group | Protection ratio | MF litter adjusted | MF Lower confidence level | Litter adjusted percent lung lesion score | LCL lung lesion score | Standard deviation of lung lesion | Mean percentile for lesions |
|---|---|---|---|---|---|---|---|
| Vaccinate IM single dose | 1/23 | 58.4% | 31% | 8.84% | 6.68% | 4.99 | 0.38 |
| Vaccinate IM double dose | 4/19 | 71.2% | 48.7% | 6.62% | 4.37% | 4.67 | 0.3 |
| Control | 0/23 | NA | NA | 19.27% | 14.62% | 10.76 | 0.69 |

LCL = Lower Confidence Level
MF = Mitigated Fraction

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09056909B2). An electronic copy of the "Sequence Listing" will also be available from the USPTO upon request and payment of the fee set forth in 37 CFR 1.19(b)(3).

What is claimed is:

1. A composition for eliciting an anti-*Mycoplasma hyopneumoniae* immune response in an animal, said composition comprising an immunologically effective amount of a live avirulent strain of *Mycoplasma hyopneumoniae* wherein the live avirulent strain of *Mycoplasma hyopneumoniae* is a J strain having ATCC accession number 25934 or an isolate thereof whose genome comprises a nucleic acid sequence having at least 95% homology to the nucleic acid sequence of SEQ ID NO.1 and the biologically acceptable adjuvant SP-Oil.

2. The composition of claim 1 wherein said SP-Oil is present at a concentration between about 1% and about 25%.

3. The composition of claim 2 wherein said SP-Oil is present at a concentration of about 10%.

4. The composition of claim 1, further comprising one or more viral antigens selected from the group consisting of a swine influenza virus (SIV) antigen, a porcine reproductive and respiratory syndrome virus (PRRSV) antigen, raccoon poxvirus expressing PRRS or other antigens, TGEV expressing PRRS or other antigens, and a porcine circovirus (PCV) antigen.

5. The composition of claim 4 wherein said one or more viral antigens comprises a Porcine Circovirus Type 1-Type 2 (cPCV1-2) chimera.

6. A method for generating an immune response to *Mycoplasma hyopneumoniae*, or for reducing at least one symptom associated with an infection by *Mycoplasma hyopneumoniae*, said method comprising the step of administering to an animal a composition according to claim 1.

7. The method of claim 6 wherein the step of administering is achieved by parenteral administration.

8. The method of claim 7 wherein the parenteral administration step is achieved by intramuscular injection.

9. The method of claim 6 wherein the step of administering is achieved by oral administration.

10. The method of claim 9 wherein the oral administration step is achieved by hand delivery or mass application.

11. The method of claim 6 wherein the step of administering is achieved by nasal administration.

12. The method of claim 6 wherein said animal is a pig.

13. The composition of claim 1, wherein the composition is an immunogenic composition.

14. The immunogenic composition of claim 13 wherein said SP-Oil is present at a concentration between about 1% and about 25%.

15. The immunogenic composition of claim 14 wherein said SP-Oil is present at a concentration of about 10%.

16. The immunogenic composition of claim 13, further comprising one or more viral antigens selected from the group consisting of a swine influenza virus (SIV) antigen, a porcine reproductive and respiratory syndrome virus (PRRSV) antigen, Raccoon Poxvirus expressing PRRS or other antigens, TGEV expressing PRRS or other antigens, and a porcine circovirus (PCV) antigen.

17. The immunogenic composition of claim 16 wherein said one or more viral antigens comprises a Porcine Circovirus Type 1-Type 2 (cPCV1-2) chimera.

18. A method for enhancing an immune response to *Mycoplasma hyopneumoniae*, said method comprising the step of administering a single or multiple doses of an immunogenic composition to an animal according to claim 13.

19. The method of claim 18, wherein the live avirulent strain of *Mycoplasma hyopneumoniae* is a *Mycoplasma hyopneumoniae* J strain designated as ATCC accession number 25934 or 27715.

20. The method of claim 19, wherein the live avirulent strain of *Mycoplasma hyopneumoniae* is a *Mycoplasma hyopneumoniae* J strain designated as ATCC accession number 27715.

21. A method for enhancing an immune response to *Mycoplasma hyopneumoniae*, said method comprising the steps of:
a) at a first time, administering a first immunogenic composition according to claim 1 comprising an immunologically effective amount of a live avirulent *Mycoplasma hyopneumoniae* strain adjuvanted with a biologically acceptable adjuvant material to an animal;
b) at a second time, administering a second immunogenic composition according to claim 1 comprising an immunologically effective amount of a live avirulent *Mycoplasma hyopneumoniae* adjuvanted with a biologically acceptable adjuvant material to an animal.

22. The method of claim 21 wherein the isolate of ATCC accession number 25934 is a strain having ATCC accession number 27715.

23. The composition of claim 1, wherein the isolate of ATCC accession number 25934 is a strain having ATCC accession number 27715.

* * * * *